United States Patent [19]
Gelvin et al.

[11] Patent Number: 4,954,442
[45] Date of Patent: Sep. 4, 1990

[54] OPINE ENHANCEMENT OF VIR GENE INDUCTION

[75] Inventors: Stanton B. Gelvin, West Lafayette, Ind.; K. Veluthambi, Madurai, India

[73] Assignee: Purdue Research Foundation, West Lafayette, Ind.

[21] Appl. No.: 239,183

[22] Filed: Aug. 31, 1988

[51] Int. Cl.$^5$ .................... C12N 15/63; C12N 15/84; A01H 1/06; A01H 4/00
[52] U.S. Cl. .......................... 435/172.3; 435/252.2; 435/253.6; 435/317.1; 435/240.4; 800/205; 800/DIG. 63; 935/35; 935/36; 935/38; 935/39; 935/43; 935/55; 935/56
[58] Field of Search ..................... 935/35, 36, 38, 39, 935/43, 55, 56; 435/252.2, 253.6, 172.3, 317.1, 240.4; 800/205, DIG. 63

[56] References Cited
U.S. PATENT DOCUMENTS
4,459,355 7/1984 Cello et al.

OTHER PUBLICATIONS

Annik Petit, Chantal David, Gary A. Dahl, Jeffrey G. Ellis, Pierre Guyon, Francine Casse-Delbart, and Jacques Tempe, "Further Extension of the Opine Concept: Plasmids in *Agrobacterium rhizogenes* Cooperate for Opine Degradation", Mol Gen Genet, (1983), 190:204–214.

Karen Whiteman Runs Him, Rudy J. Scheffer, and Gary A. Strobel, "Factors Influencing Root Formation in Dicots by *Agrobacterium rhizogenes*", CAN, J. Bot., vol. 66, 1988.

Shahla N. Sheikholeslam and Donald P. Weeks, "Acetosyringone Promotes High Efficiency Transformation of *Arabidopsis thaliana* Explants by *Agrobacterium tumefaciens*", Plant Molecular Biology 8:291–298, (1987).

Alt-Moerbe et al., (Jul. 1988), Mol. ben. benet. 213:1–8.
Colak et al., (1980), Phytopathologische Zeitschrift 99:81–86, (Chem. Abstract date: Nov. 24, 1980).
Janssens et al., (1986), Plant Science 47:185–193.
Chilton et al., (1985), Phytochemistry 24:221–224.
Chilton et al., (1984), Biochemistry 23:3290–3297.
Djordjevic et al., (1987), The EMBO Journal 6:1173–1179.

Primary Examiner—Charles F. Warren
Assistant Examiner—Barbara M. Chereskin
Attorney, Agent, or Firm—Barnes & Thornburg

[57] ABSTRACT

Transcription of the vir genes of the Ti-plasmid in Agrobacterium species, typically induced by phenolic compounds secreted by wounded plant cells, is enhanced when induction is carried out in the presence of effective amounts of an opine from the Octopine Family of Nopaline Family. Production of T-strands in Agrobacterium species can be potentiated by induction preferably in the presence of octopine, nopaline, succinamopine, or leucinopine. Agrobacterium species induced in the presence of an opine compound of the Nopaline or Octopine Family effect highly efficient transformation of even recalcitrant plant species.

13 Claims, No Drawings

OPINE ENHANCEMENT OF VIR GENE INDUCTION

This invention relates to an improved method for using genetically engineered Agrobacterium species to transform plant cells. More particularly, this invention is directed to a method for potentiating T-strand production in Agrobacterium species and thereby enhancing the capacity of said Agrobacterium species to infect plant tissue and transform constituent cells. The method comprises inducing vir gene transcription in an Agrobacterium species in the presence of an effective amount of an opine of the Octopine Family or the Nopaline Family.

BACKGROUND AND SUMMARY OF THE INVENTION

*Agrobacterium tumefaciens* causes the disease crown gall in most species of dicotyledonous plants and on some monocots and gymnosperms. Virulent strains of the bacterium contain one of the large class plasmids termed Ti-(tumor inducing) plasmids. During the infection process a portion of the Ti-plasmid, the T-(transferred) DNA, is transferred from the bacterium to the plant where it is covalently incorporated into the nuclear DNA and is expressed in the living plant cell. Among the products encoded by the T-DNA in plant cells are enzymes involved in the production of the phytohormones auxin and cytokinin, and enzymes involved in the production of unusual low molecular weight compounds called opines. The production of large quantities of phytohormones, directed by the T-DNA, results in the uncontrolled proliferation of plant tissue leading to the growth of crown gall tumors. Opines made by and secreted from these tumors are utilized by the inciting bacteria as a carbon and sometimes a nitrogen source. Thus the transfer to and the expression of the T-DNA in plant cells allows Agrobacterium species to genetically engineer the host plant to make compounds (the opines) that, with a few exceptions, only it can utilize. The bacterium thereby creates a niche for itself in the rhizosphere.

The Agrobacterium system represents a natural situation by which genes are transferred from a bacterium to a plant cell. This system has therefore been modified in many laboratories to deliver novel gene combinations to plant cells, and as such, is currently the most efficient way to transfer foreign genes into the genome of certain plant species. Thus the T-DNA region of the Ti-plasmid of an Agrobacterium species is modified utilizing art-recognized recombinant DNA techniques to delete tumor inducing genes and to include inserted foreign genes coding for proteins and protein systems which, when expressed, imparts favorable phenotypic characteristics to the modified plant species.

The molecular events leading to the excision of the T-DNA from the Ti-plasmid and the transfer and integration of the T-DNA into plant cells is still poorly understood. It is known, however, that the process is initiated when the bacterium species receives certain "chemical signals" from the wounded plant cell. Among the chemicals exuded by wounded plant tissue are phenolic compounds, including acetosyringone. The bacterium responds to such chemicals by activating certain genes called vir genes, on the Ti-plasmid. Among the compounds encoded and expressed by the induced vir genes is an endonuclease that is involved in the excision of T-DNA from the Ti-plasmid. Upon induction by one or more signal compounds from wounded plant cells, single-stranded DNA derived from the T-region of the Ti-plasmid can be found in the Agrobacterium. These molecules, termed T-strands, have been proposed to be the intermediate molecules that are transferred to the plant cells from the bacterium. This model is based upon the mechanism by which bacteria mate, or conjugate, plasmids with other bacteria. The transfer of the T-DNA from Agrobacterium to plant cells has therefore been likened to the transfer of DNA between bacterial cells.

The Agrobacterium system plays a crucial role in present day research and development efforts in the area of plant genetics. Yet, the Agrobacterium system has its inherent limitations. Transformation efficiencies are not always what plant scientists would like them to be. Moreover, there are may so-called recalcitrant plant species which are difficult to transform utilizing the Agrobacterium system. A method for enhancing plant cell transformation efficiency would have many positive implications for plant genetic engineering.

Therefore, it is an object of this invention to provide an improved method for inducing Agrobacterium species to infect plant cells and to transfer T-DNA to the plant cells for expression therein.

It is another object of this invention to provide an improved method for inducing transcription of the vir genes of the Ti-plasmid in an Agrobacterium species to produce elevated levels of T-strands in said species.

A further object of this invention to provide an improved method for transforming plant cells by infecting said cells with genetically engineered Agrobacterium species having potentiated levels of T-strands.

Still another object of this invention is to provide a novel induction medium for Agrobacterium species for enhancing the capacity of said species to infect and transform plant cells.

In accordance with this invention, there is provided a method for potentiating the induced transcription of vir genes on Ti-plasmids in Agrobacterium species to provide enhanced levels of T-strands and concomitantly an enhanced capacity for transformation of plant cells. When induced in accordance with this invention, Agrobacterium species having Ti-plasmids genetically engineered to contain T-DNA genes for expression in plants to produce favorable phenotypic characteristics, can effect high efficiency transformation of even art-recognized recalcitrant plant species. Opines of the Nopaline and Octopine Family have been found to potentiate the art-recognized induction of vir genes on Ti-plasmids of Agrobacterium species in the presence of compounds released by injured plant tissue, including phenolic vir gene inducers such as acetosyringone.

Phenolic compounds secreted by wounded plant cells can induce the activity of certain genes encoded by the Ti-plasmid of Agrobacterium tumefaciens and other Agrobacterium species. These inducible genes include the so-called vir genes that function in the process of T-DNA excision and transfer and the gene pinF of unknown function. The induction process is mediated by the genes virA and virG. VirA is a constitutively active gene and encodes an inner membrane-localized protein that most likely functions as the receptor for phenolic inducers such as acetosyringone. The virG locus, also constitutively active at a low level, is subsequently induced to higher levels of expression and presumably encodes a transcriptional activator that induces the genes virB, virC, virD, virE, virG and pinF. The virD locus encodes a T-DNA border-specific endonuclease that nicks the T-DNA border repeat sequences on the bottom strand generating single-stranded T-DNA molecules called "T-strands." T-strands can be coated with a virE-encoded DNA binding protein and have been hypothesized to be the form of the T-DNA transferred to the plant cell during infection/transformation by Agrobacterium species. The virD endonuclease also generates double stranded scissions of the T-DNA borders.

Opines have been categorized into several "families" including the Octopine Family, the Nopaline Family, the Agropine Family and the Agrocinopine Family. Exemplary of compounds belonging to the Nopaline Family are compounds of the general formula:

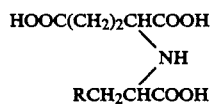

wherein R is selected from the group consisting of 2-guanidinylethyl (nopaline): 2-aminoethyl (nopalinic acid); isopropyl (leucinopine); and carbamoyl (succinamopine). Compounds in the Octopine Family are similar to the those in the Nopaline Family in that they have the imino diacid structure —CH(COOH)NHCH(COOH)—. Exemplary compounds of the Octopine Family are compounds of the structure

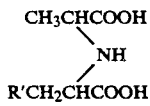

wherein R' is selected from the group consisting of 2-guanidinylethyl (octopine); 2-aminoethyl (octopinic acid); 3-aminopropyl (lysopine); and 4-imidazolyl (histopine).

Opines belonging to the Agropine Family and the Agrocinopine Family do not have the imino diacidic structure common to the Octopine and Nopaline Families. Agrocinopines are phosphorylated sugars while compounds of the Agropine Family, including agropine, mannopine, mannopinic acid and agropinic acid have cyclic and acyclic structures related to agropine of the formula

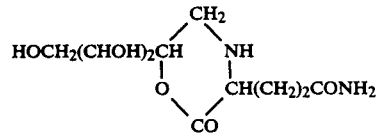

It has been found that opines in the Octopine Family and Nopaline Family potentiate the induction of vir genes in Agrobacterium tumefaciens with compounds released from injured plant tissue, including particularly acetosyringone. Mannopine, a member of the Agropine Family, and acetopine, a compound that is found in certain nontransformed plant tissues, were found not to enhance the acetosyringone induced transcription of vir genes in Agrobacterium tumefaciens. It is noted too that none of the opine compounds tested to date induced vir gene transcription alone. The significant potentiation of vir gene induction with opines in the Nopaline and Octopine Families have been observed only in the presence of acetosyringone and other compounds released from wounded plant species. Among the opines that have been demonstrated to potentiate induced vir gene transcription are octopine, leucinopine, succinamopine and nopaline (in order of increasing potentiating effect).

TABLE 1

EFFECT OF OPINES ON THE INDUCTION OF VIR GENES*

| | $\beta$-Galactosidase Units | | | |
|---|---|---|---|---|
| | virB | | pinF | |
| Treatments | −AS | +AS | −AS | +AS |
| K3 medium | N.D. | 27 ± 0.5 | 5 ± 0.4 | 160 ± 7.0 |
| K3 + Octopine | N.D. | 143 ± 2.4 | 16 ± 0.5 | 370 ± 5.0 |
| K3 + Nopaline | N.D. | 343 ± 2.0 | 17 ± 0.5 | 829 ± 30 |
| K3 + Succinamopine | N.D. | 100 ± 1.3 | 34 ± 2.0 | 450 ± 11 |
| K3 + Leucinopine | N.D. | 216 ± 9.3 | 32 ± 2.4 | 487 ± 19 |
| K3 + Mannopine | N.D. | 18 ± 0.6 | 16 ± 0.5 | 176 ± 7.0 |

*AS = Acetosyringone, 30 μM
All opines at 10 mM
N.D. = Not detected

TABLE 2

EFFECT OF OPINES AND RELATED COMPOUNDS ON VIR GENE INDUCTION

| | virB | | | pinF | | |
|---|---|---|---|---|---|---|
| Treatments** | −AS* | +AS | Fold increase over AS | −AS | +AS | Fold increase over AS |
| K3 Control | 0.9 | 5.0 | — | 9.8 | 126 | — |
| K3 + Octopine | 1.5 | 58.0 | 11.6 | 17.4 | 365 | 2.9 |
| K3 + Nopaline | 2.6. | 189.0 | 37.8 | 40.0 | 808 | 6.4 |
| K3 + Arginine | 1.7. | 27.0 | 5.4 | 6.1 | 167 | 1.3 |
| K3 + Leucine | 0.9. | 13.4 | 2.7 | 5.3 | 161 | 1.3 |
| K3 + Pyruvate | 1.8. | 7.3 | 1.5 | 14.4 | 109 | — |

*AS = 0.03 mM acetosyringone
**Opines and other compounds at 10 mM

Thus, opines can be applied in effective concentrations with the Agrobacterium species to injured plant tissue to enhance transformation efficiency. Alternatively, and preferably, the Agrobacterium species is induced in a medium containing, for example acetosyringone and an opine from the Octopine or Nopaline Families in amounts effective to potentiate vir gene transcription and concomitant T-strand production in the induced bacterium species, prior to exposure of said induced species to plant cells targeted for transformation.

Effective concentrations of acetosyringone in an induction medium for use in accordance with the present invention range from about 1 μM to about 50 μM. Higher concentrations of acetosyringone can be used without advantage. Opine concentrations found effective to potentiate acetosyringone and induce transcription of vir genes in Agrobacterium species range from about 1 mM to about 50 mM, more preferably between about 5 mM and about 30 mM. As with acetosyringone, higher concentrations of the opine can be utilized but without advantage. The preferred concentration of opine for potentiating induced vir gene transcription in Agrobacterium species depends on the identity of the opine, the Agrobacterium species and strain and, to some extent, the concentration of acetosyringone or other chemical signal compound emanated by injured plant tissue.

While the experimental examples set forth herein below were conducted with strains of *Agrobacterium tumefaciens*, a preferred Agrobacterium species inducible in accordance with the present invention, other Agrobacterium species containing Ti-plasmids, such as *Agrobacterium rhizogenes* and *Agrobacterium rubi* are expected to respond similarly when induced in accordance with the present invention.

Also within the scope of this invention is a composition comprising acetosyringone and an opine compound of the Octopine Family or the Nopaline Family in an amount effective to potentiate acetosyringone induced transcription of vir genes in Agrobacterium species. The composition can be formulated in the form of an induction medium which includes, in addition, a minimal medium conducive to the viability of Agrobacterium species over a period of time sufficient to allow potentiated vir gene induction in said Agrobacterium species. Thus, for example, an induction medium can be formulated by adding effective amounts of acetosyringone and nopaline to art-recognized K3 medium, preferably buffered with sodium phosphate or sodium citrate, for example, to a pH of about 5.4 to about 5.6. The concentrations of acetosyringone can range from about 1 μM to about 50 μM and the concentration of opine compound can range from about 1 mM to about 50 mM.

Characterization of Acetosyringone Induction

*Agrobacterium tumefaciens* strain A348mx219 was used to characterize the induction of Ti-plasmid genes by acetosyringone. That strain contains the lacZ-fusion transposon Tn3-HoHol inserted into the gene pinf. Although pinF is not involved in virulence, its transcription is inducible by acetosyringone and co-cultivation with plant protoplasts in a manner similar to that of many other vir genes. Further, beta-galactosidase activity is high relative to that seen following the induction of other vir genes; thus pinF is a useable reporter of acetosyringone inducibility. Induction of the pinF gene in *Agrobacterium tumefaciens* strain A348mx219 was observed at acetosyringone concentrations as low as 3 μM, and induction was found to be maximal at 30 μM acetosyringone. Those concentrations were therefore used in the following described experiments for limiting (3 μM) or saturating (30 μM) induction conditions. Induction of the pinF gene can be definitively observed as early as 6 hours following incubation with acetosyringone. The effect is maximal approximately 36 hours following induction. Accordingly, an induction time of 24 hours was selected to perform most of the experiments described below. The kinetics of inductions and the concentration of acetosyringone necessary for limiting and maximal induction are similar to those previously reported in the literature.

Effective of Opines Upon pinF and vir gene induction

*A. tumefaciens* strain A348mx219 was incubated with 30 μM acetosyringone for 24 hours in K3 medium in the presence/absence of 10 mM octopine. The expression of pinF (as determined by beta-galactosidase activity) was 2.3-fold greater in the presence of octopine than in its absence. This induction by octopine was dependent upon the presence of acetosyringone. Octopine alone did not induce pinF. The potentiation of pinF gene induction by octopine in the presence of acetosyringone is approximately linear in the octopine concentration range investigated (2–40 mM).

The effect of octopine upon acetosyringone induction of each vir gene in derivatives of *Agrobacterium tumefaciens* strain A348 was investigated. Those strains harbor Tn3-HoHol insertions in different vir genes. The beta-galactosidase activity in these strains under various incubation conditions were monitored. Each of the strains except A348mx365 (virC::Tn3-HoHol), contained a lacZ-fusion in the sole relevant vir gene harbored by the bacterium. Because strain A348mx365 showed only low levels of induction by acetosyringone, the merodiploid strain A348(pSM365), harboring multiple copies of the cosmid pSM365 was used to monitor virC induction.

Table 3 shows that the activity of virB, virC, virD and virE in acetosyringone induced cells was 3.2- to 5.4-fold higher in the presence of 10 mM octopine than in its absence. As with the induction of pinF, octopine alone did not induce any of the vir genes. Activity of virA was not affected by either acetosyringone or octopine. The constitutive expression of this virA::Tn-3HoHol fusion gene in *Agrobacterium tumefaciens* has been previously demonstrated and reported in the literature.

TABLE 3

INDUCTION OF VIR and PINF LOCI BY ACETOSYRINGONE AND OCTOPINE

| | β-Galactosidase units | | | | | Fold Induction | |
|---|---|---|---|---|---|---|---|
| Locus | AB | K3 | K3 + OCT | K3 + AS | K3 + AS + OCT | AS/ K3 | AS + OCT/ AS |
| pinF | N.D. | 7.4 | 10.4 | 148.0 | 332.0 | 20.0 | 2.3 |
| virA | 13.4 | 18.3 | 18.9 | 18.1 | 20.0 | NIL | NIL |
| virB | N.D. | 0.6 | 0.6 | 13.0 | 70.1 | 22.0 | 5.4 |
| virG | 14.4. | 41.0 | 54.1 | 38.2 | 54.1 | NIL | 1.4** |
| virC* | N.D. | 2.5 | 3.8 | 8.2 | 30.7 | 3.3 | 3.7 |
| virD | N.D. | 1.4 | 1.8 | 13.8 | 44.3 | 10.0 | 3.2 |

TABLE 3-continued

| | INDUCTION OF VIR and PINF LOCI BY ACETOSYRINGONE AND OCTOPINE | | | | | |
|---|---|---|---|---|---|---|
| | β-Galactosidase units | | | | Fold Induction | |
| Locus | AB | K3 | K3 + OCT | K3 + AS | K3 + AS + OCT | AS/ K3 | AS + OCT/ AS |
| virE | N.D. | 12.7 | 14.7 | 26.6 | 133.0 | 2.1 | 5.0 |

*A348(pSM365), a merodiploid, was used.
N.D. = Not detected
**Induction by octopine was AS-independent
AS = 0.03 mM acetosyringone
OCT = 10 mM octopine The activity of virG was induced by incubation of the bacteria in K3 medium. No significant further induction of virG was seen in the presence of either acetosyringone, octopine, or both. The lack of further induction of virG can be explained by the fact that the only copy of the gene has been disrupted in this strain. The virG gene product most likely functions as a transcriptional activator of itself, the other vir genes and pinF, and this strain therefore would not contain active virG protein.

Table 2 shows that neither arginine nor pyruvate, the compounds from which octopine is formed, nor the neutral amino acid leucine stimulate the acetosyringone induction of either virB or pinF Surprisingly, nopaline had a greater effect upon the acetosyringone induction of these genes than did octopine. Neither the Ti-plasmid harbored by *Agrobacterium tumefaciens* strain A348(pTiA6) nor the chromosome in this strain (C58 chromosomal background) encode functions that allow the catabolism of nopaline. Enhancement of the acetosyringone induction of pinF by nopaline, as with octopine, is not yet saturated at 10 mM concentration of the opine.

With the observation of the stimulation of acetosyringone induction of the vir genes and pinF by an opine that is not catabolized by this strain of Agrobacterium, the effects of other opines were tested. Table 1 shows that mannopine, an opine that is catabolized by this bacterial strain, does not stimulate acetosyringone induction of virB or pinF. Succinamopine and leucinopine, at 10 mM, do stimulate this induction. Neither of these opines are catabolized by the subject Agrobacterium strain.

Involvement of virA and virG in the Opine Enhancement phenomenon

Because the transposon Tn3-HoHoI acts not only as a reporter of gene activity but also as an insertional mutagen, the data in Table 3 suggests that the genes virB, virD, virE and pinF are not involved in the phenomenon of opine enhancement of vir gene induction. This is because the only copy of these genes has been disrupted in the relevant strains, yet octopine could still stimulate the acetosyringone induction of these genes. The participation of the gene virC in this process is possible for the merodiploid strain A348(pSM365), harboring an intact copy of virC was employed. The participation of the genes virA and virG in the opine enhancement phenomenon was ambiguous because of the disruption of these genes would not permit acetosyringone induction.

To clarify the involvement of the genes virA, virG and possibly virC and to eliminate the necessity of most other Ti-plasmid encoded genes for this process, plasmid pSM405 was introduced into the Agrobacterium strain A136. This Agrobacterium strain contains the same chromosomal background as does the strain A348, but lacks any Ti-plasmid. The plasmid pSM405 contains a Tn3-HoHoI transposon in the 5' end of the virB locus harbored by the cosmid pVK257. This cosmid harbors the genes pinF, virA, virB, virC and the first two open reading frames of the virD locus. Table 4 shows that the acetosyringone induction of the virB locus in the strain A136(pSM405) could be enhanced 3-fold by 10 mM nopaline. Because the first two open reading frames of the virD locus encode a T-DNA border-specific endonuclease, it is likely that the stimulation of the acetosyringone induction of vir genes is mediated through the genes virA and virG. These experiments do not rule out the possibility of a role for virC and chromosomal genes in this process.

TABLE 4

| | EFFECT OF VIR GENES ON THE NOPALINE STIMULATION OF VIR GENE ACTIVITY | | | | |
|---|---|---|---|---|---|
| | | | β-Galactosidase units[a] | | |
| | Gene disrupted by Tn3-HoHoI | Wild-Type vir genes present in the bacterium | K3 medium | K3 medium + acetosyringone | K3 medium + acetosyringone + nopaline |
| A348mx219 | pinF | A, B, C, G, D, E | 0 | 43 | 280 |
| A348mx243 | virB | A, C, G, D, E | 0 | 3.3 | 60 |
| A136(pSM405) | virB | A, C, G | 0 | 20 | 66 |

[a]β-Galactosidase activity was measured following incubation at 20° C. for 24 hrs.

Effect of Opines on T-strand synthesis and T-DNA border cleavage

It is reported in the literature that upon acetosyringone induction of *Agrobacterium tumefaciens* cells, single-stranded T-DNA molecules, termed T-strands, accumulate in the bacteria. All possible combinations of the four T-DNA borders can be used to generate T-strands of different sizes in *Agrobacterium tumefaciens* strain A348. The first two open reading frames in the virD region encode proteins involved in the site-specific productions of nicks in the bottom strand of the T-DNA borders, leading to the production of T-strands. The proteins encoded by these two open reading frames also catalyze the double-stranded cleavage of the T-DNA at these border sequences. Because octopine and nopaline enhance the acetosyringone-induced activity of virD, the capacity of these opines to stimulate the ability of acetosyringone to induce both the production of T-strands and the double-stranded cleavage of the T-DNA at border A was tested.

Utilizing the probe, HindIII fragment Y, it was determined that using acetosyringone only at limiting concentrations, T-strands could not be detected unless 5 mM nopaline was included in the incubation solution. The use of 30 μM acetosyringone without nopaline resulted in approximately the same level of T-strand accumulation as did 3 μM acetosyringone plus 5 mM nopaline. Inclusion of nopaline in the incubation solution resulted in the increased accumulation of both the A-B and A-C T-strands. At saturating acetosyringone concentrations, nopaline greatly stimulates the accumulation of single-stranded DNA fragments in the bacterium. Thus, nopaline enhances the ability of acetosyringone to induce both T-strands and the double-stranded cleavage of the T-DNA borders. Similar results were obtained using octopine instead of nopaline.

Effect of Nopaline and Acetosyringone on plant Transformation

Although it was shown that opines such as nopaline and octopine enhance induction of certain vir genes, the production of T-strands and the double-stranded cleavage of the T-DNA borders, there was still a need to demonstrate whether or not nopaline could enhance the transformation of plants with Agrobacterium species. *Gossypium hirsutum* (cotton) shoot apices were infected with *Agrobacterium tumefaciens* strain LBA4404 containing a T-DNA binary vector harboring a beta-glucuronidase (GUS) gene. Following 4 to 7 weeks in culture, tissues from the newest regenerated leaves were assayed for GUS activity using a fluorimetric assay.

Table 5 shows that neither non-transformed plants nor plants transformed in the presence of 30 mM nopaline displayed GUS activity. Infection of apices in the presence of 10 μM acetosyringone yielded two GUS positive transformants out of 47 (3.5%) plants tested. Infection in the presence of nopaline plus acetosyringone, however, yielded 37 out of 45 GUS positive plants (82%). Thus, incubation of Agrobacterium cells in the presence of acetosyringone plus nopaline significantly enhances the transformation of cotton.

TABLE 5

TRANSFORMATION OF COTTON SHOOT APICES BY *A. TUMEFACIENS* STRAIN LBA4404(pRGUS2)

| Treatment[a] | Number of shoot apices cultured | Number of shoot apices assayed | Number of GUS positive plants[b] | % GUS positive plants |
|---|---|---|---|---|
| None | 1298 | 93 | 0 | 0 |
| Nopaline | 60 | 49 | 0 | 0 |
| Acetosyringone | 65 | 57 | 2 | 3.5 |
| Nopaline + Acetosyringone | 60 | 45 | 37 | 82 |

[a]Nopaline was used at 30 mM. Acetosyringone was used at 10 μM. These chemicals were dissolved in DMSO and applied to the shoot apex at the time of innoculation.
[b]A fluorimetric assay using 4-methyl umbelliferyl glucoronide was employed. The fluorescent methyl umbelliferone product was visualized after 24 hours on a 365 nm UV light box.

We claim:

1. In a method for genetically transforming plant cells by infecting said cells with a genetically engineered Agrobacterium species characterized by an acetosyringone mediated induction of Ti-plasmid vir gene transcription, the improvement which comprises the steps of inducing vir gene transcription of Ti-plasmids in the genetically engineered Agrobacterium species with acetosyringone in the presence of an effective induction enhancing amount of an opine from the Octapine family or Nopaline family to promote production of T-strand DNA in said induced species, and thereafter infecting the plant cells with an inoculum comprising the vir gene induced Agrobacterium species.

2. The improvement of claim 1 wherein the opine is an imino diacid of the formula

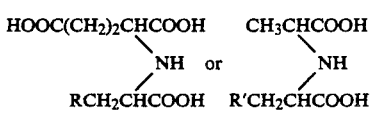

wherein R is selected from the group consisting of carbamoyl, isopropyl, 2-guanidinylethyl and 2-aminoethyl; and R' is selected from the group consisting of 2-guanidinylethyl, 2-aminoethyl, 3-aminopropyl and 4-imidazolyl.

3. The improvement of claim 2 wherein R is carbamoyl, isopropyl or 2-guanidinylethyl and R' is 2-guanidinylethyl.

4. The improvement of claim 1 wherein the opine is nopaline.

5. The improvement of claim 1 wherein the opine is succinamopine.

6. The improvement of claim 1 wherein the opine is leucinopine.

7. In a method for transforming plant cells by infecting said cells with genetically engineered Agrobacterium species induced to infect said cells in the presence of acetosyringone, the improvement which comprises inducing said Agrobacterium species with acetosyringone in the presence of a transformation enhancing amount of an opine compound of the formula

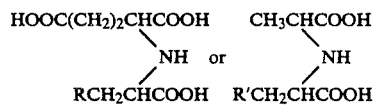

wherein R is selected from the group consisting of carbamoyl, isopropyl, 2-guanidinylethyl and 2-aminoethyl; and R' is selected from the group consisting of 2-guanidinylethyl, 2-aminoethyl, 3-aminopropyl and 4-imidazolyl, provided that said opine compound is not catabolized by said Agrobacterium species.

8. The improvement of claim 7 wherein the Agrobacterium species is *Agrobacterium tumefaciens*.

9. The improvement of claim 7 wherein the opine is selected from the group consisting of octopine, nopaline, leucinopine, and succinamopine.

10. A medium for promoting enhanced vir gene induction in Agrobacterium species characterized by acetosyringone mediated vir gene induction, to enhance levels of T-strand DNA in said bacterium, said medium comprising acetosyringone at a concentration of about 1 μm to about 50 μm and an opine compound of the formula

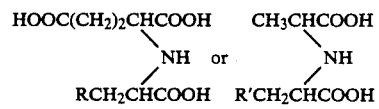

wherein R is selected from the group consisting of carbamoyl, isopropyl, 2-guanidinylethyl and 2-aminoethyl; and R' is selected from the group consisting of 2-guanidinylethyl, 2-aminoethyl, 3-aminopropyl and 4-imidazolyl, said opine at a concentration of about 1 mM to about provided that the opine is not catabolized by the Agrobacterium species 50 mM.

11. The composition of claim 10 where in the opine compound is selected from the group consisting of octopine, nopaline, leucinopine and succinamopine.

12. The composition of claim 10 further comprising nutrients conducive to the viability of Agrobacterium species.

13. The composition of claim 12 comprising acetosyringone and an opine in K3 medium buffered to a pH of about 5.4 to about 5.6.

* * * * *

UNITED STATES PATENT AND TRADEMARK OFFICE
CERTIFICATE OF CORRECTION

PATENT NO. : 4,954,442

DATED : September 4, 1990

INVENTOR(S) : Gelvin et al.

It is certified that error appears in the above-identified patent and that said Letters Patent is hereby corrected as shown below:

In column 1, line 16, please insert a new paragraph as follows:
--This Invention was made with Government support under Contract No. 88-133-DMB-83-51152 awarded by the National Science Foundation. The Government has certain rights in this invention.--

In column 6, line 20, replace "Effective" with --Effect--.

In column 7, line 25, after "pinF", please insert --.--.

Signed and Sealed this

Thirty-first Day of March, 1992

Attest:

HARRY F. MANBECK, JR.

*Attesting Officer*  *Commissioner of Patents and Trademarks*